(12) United States Patent
Chang

(10) Patent No.: US 10,470,917 B2
(45) Date of Patent: Nov. 12, 2019

(54) MULTILAYER FILM INCLUDING ODOR BARRIER LAYER HAVING SOUND DAMPENING PROPERTIES

(71) Applicant: Hollister Incorporated, Libertyville, IL (US)

(72) Inventor: Moh-Ching Oliver Chang, Lake in the Hills, IL (US)

(73) Assignee: Hollister Incorporated, Libertyville, IL (US)

(*) Notice: Subject to any disclaimer, the term of this patent is extended or adjusted under 35 U.S.C. 154(b) by 417 days.

(21) Appl. No.: 15/301,829

(22) PCT Filed: May 21, 2015

(86) PCT No.: PCT/US2015/031954
§ 371 (c)(1),
(2) Date: Oct. 4, 2016

(87) PCT Pub. No.: WO2015/199852
PCT Pub. Date: Dec. 30, 2015

(65) Prior Publication Data
US 2017/0042722 A1    Feb. 16, 2017

Related U.S. Application Data

(60) Provisional application No. 62/016,355, filed on Jun. 24, 2014.

(51) Int. Cl.
*A61F 5/441* (2006.01)
*B32B 27/34* (2006.01)
(Continued)

(52) U.S. Cl.
CPC .......... *A61F 5/441* (2013.01); *B32B 7/00* (2013.01); *B32B 7/02* (2013.01); *B32B 7/12* (2013.01);
(Continued)

(58) Field of Classification Search
CPC ................................................ A61F 5/441
See application file for complete search history.

(56) References Cited

U.S. PATENT DOCUMENTS 4,946,720 A * 8/1990 Oishi ............... A61F 5/445
428/35.4
4,983,171 A * 1/1991 Schirmer ........... A61F 5/445
604/332
(Continued)

FOREIGN PATENT DOCUMENTS

EP    1101605 A2    5/2001
EP    1598180 A1    11/2005
(Continued)

OTHER PUBLICATIONS

Kato, Kiyoo, Recent Advances in Thermoplastic Elastomer in Japan, Journal of the Society of Rubber Science and Technology, 2007, pp. 226-232, vol. 80, No. 6. Japan.

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

A multilayer film including an odor barrier layer having sound dampening properties is provided. The odor barrier layer is formed from a polyamide modified with a functionalized vinyl-bond rich triblock copolymer.

14 Claims, 2 Drawing Sheets

(51) Int. Cl.
*C08G 81/02* (2006.01)
*B32B 7/00* (2019.01)
*B32B 7/02* (2019.01)
*B32B 7/12* (2006.01)
*B32B 27/06* (2006.01)
*B32B 27/08* (2006.01)
*B32B 27/28* (2006.01)
*B32B 27/30* (2006.01)
*B32B 27/32* (2006.01)
*B32B 27/38* (2006.01)

(52) U.S. Cl.
CPC ............ *B32B 27/06* (2013.01); *B32B 27/08* (2013.01); *B32B 27/28* (2013.01); *B32B 27/30* (2013.01); *B32B 27/302* (2013.01); *B32B 27/306* (2013.01); *B32B 27/308* (2013.01); *B32B 27/32* (2013.01); *B32B 27/34* (2013.01); *B32B 27/38* (2013.01); *C08G 81/021* (2013.01); *C08G 81/022* (2013.01); *B32B 2250/00* (2013.01); *B32B 2250/05* (2013.01); *B32B 2250/24* (2013.01); *B32B 2307/10* (2013.01); *B32B 2307/102* (2013.01); *B32B 2307/70* (2013.01); *B32B 2307/7248* (2013.01); *B32B 2439/00* (2013.01); *B32B 2439/06* (2013.01); *B32B 2439/46* (2013.01); *B32B 2439/80* (2013.01); *B32B 2535/00* (2013.01)

(56) References Cited

U.S. PATENT DOCUMENTS

| | | | | |
|---|---|---|---|---|
| 5,895,694 | A * | 4/1999 | Zavadsky | A61F 5/445 428/36.7 |
| 6,143,383 | A * | 11/2000 | Giori | A61L 28/0015 428/35.2 |
| 6,179,818 | B1 * | 1/2001 | Kydonieus | A61F 5/445 604/332 |
| 6,258,423 | B1 * | 7/2001 | Giori | A61F 5/445 428/220 |
| 6,455,161 | B1 * | 9/2002 | Regnier | B32B 27/28 428/412 |
| 6,617,490 | B1 * | 9/2003 | Chen | A61F 13/15707 604/379 |
| 6,673,982 | B1 * | 1/2004 | Chen | A61F 13/4751 604/378 |
| 7,270,860 | B2 | 9/2007 | Giori | |
| 8,399,077 | B1 * | 3/2013 | Bekele | A61F 5/44 428/35.2 |
| 2002/0132071 | A1 * | 9/2002 | Buongiorno | A61L 28/0026 428/35.2 |
| 2003/0064182 | A1 * | 4/2003 | Giori | B32B 27/32 428/35.2 |
| 2003/0218022 | A1 * | 11/2003 | Chomik | A47K 11/02 220/495.02 |
| 2004/0228992 | A1 * | 11/2004 | Giori | A61F 5/445 428/35.7 |
| 2005/0079372 | A1 * | 4/2005 | Schmal | B32B 27/08 428/482 |
| 2005/0273064 | A1 * | 12/2005 | Dircks | B32B 7/12 604/322 |
| 2009/0286909 | A1 * | 11/2009 | Shibutani | C08L 29/04 524/114 |
| 2011/0112492 | A1 * | 5/2011 | Bharti | A61M 1/0088 604/319 |
| 2011/0125114 | A1 * | 5/2011 | Bekele | A61F 5/445 604/332 |
| 2012/0232504 | A1 * | 9/2012 | Chang | A61F 5/445 604/332 |
| 2013/0025764 | A1 * | 1/2013 | Henderson | A01N 25/10 156/60 |
| 2013/0035653 | A1 * | 2/2013 | Kannankeril | A61F 5/441 604/333 |
| 2013/0096521 | A1 * | 4/2013 | Bekele | A61F 5/44 604/333 |
| 2013/0310782 | A1 * | 11/2013 | Chang | A61F 5/441 604/333 |
| 2014/0205828 | A1 * | 7/2014 | Chang | B32B 27/065 428/220 |
| 2014/0207094 | A1 * | 7/2014 | Chang | A61L 28/0026 604/333 |
| 2014/0221950 | A1 * | 8/2014 | Chang | A61L 28/0034 604/332 |
| 2014/0221951 | A1 * | 8/2014 | Chang | A61F 5/445 604/332 |
| 2014/0371698 | A1 * | 12/2014 | Chang | A61F 5/445 604/333 |
| 2015/0030657 | A1 * | 1/2015 | Ludlow | A61L 27/3826 424/424 |
| 2015/0246509 | A1 * | 9/2015 | Bekele | B32B 27/08 428/35.4 |
| 2016/0058605 | A1 * | 3/2016 | Chang | A61F 5/445 604/332 |
| 2016/0114974 | A1 * | 4/2016 | Kurihara | B32B 27/32 383/71 |
| 2017/0042722 | A1 * | 2/2017 | Chang | B32B 7/00 |

FOREIGN PATENT DOCUMENTS

| | | |
|---|---|---|
| JP | 10272742 A | 10/1998 |
| JP | 2002347188 A | 12/2002 |
| JP | 2013509913 A | 3/2013 |
| WO | 2011056861 A1 | 5/2011 |
| WO | 2013102009 A1 | 7/2013 |

* cited by examiner

MULTILAYER FILM INCLUDING ODOR BARRIER LAYER HAVING SOUND DAMPENING PROPERTIES

CROSS-REFERENCE TO RELATED APPLICATIONS

This is a National Stage Application of International Patent Application No. PCT/US2015/031954, filed May 21, 2015, which claims the benefit of U.S. Provisional Application No. 62/016,355, filed Jun. 24, 2014, the contents of which are incorporated fully by reference herein.

BACKGROUND

The present disclosure relates to a multilayer film, and more particularly to a multilayer film including an odor barrier layer having sound dampening properties.

Ostomy appliances for collecting body waste, such as ostomy pouches, are used by patients who have had surgery such as a colostomy, ileostomy, or urostomy. It is desirable that ostomy appliances are made using a film having good odor barrier properties and that produce minimal noise when flexed or wrinkled to avoid embarrassment to users. Sound absorbing or sound dampening properties are also desirable for ostomy appliances. When body waste is released from a stoma, flatus gas is often released together with the waste. The flatus gas passing through the stoma can cause a vibratory transient in body tissue, which is uncontrollable by the patient. Such release of the flatus gas from the stoma can accompany indiscreet noise, which too can cause embarrassment to the patient. Thus, it is desirable that the film for ostomy appliances have sound absorbing properties in addition to odor barrier and quietness properties.

Chang et al., WO 2013/102009 discloses an ostomy appliance made using a sound absorbing material, such as a multilayer film including at least one layer comprising a sound absorbing triblock copolymer or a sound absorbing non-woven material comprising a sound absorbing triblock copolymer. Chang et al., U.S. patent application Ser. No. 13/837,867, discloses a sound absorbing adhesive and a film including a sound absorbing adhesive layer for ostomy appliances. Further, Chang, U.S. patent application Ser. No. 13/835,499, discloses a laminate including a sound absorbing foam layer for ostomy appliances. These patent applications are commonly signed to the assignee of the present application and incorporated herein in their entirety by reference.

Further, quiet films that make relatively low rustling noise, for example, plastic crackling sounds made by the ostomy pouch when a user moves around, have been developed. Examples of such a quiet film include multilayer films disclosed in Giori, U.S. Pat. No. 7,270,860, which is assigned to the assignee of the present application and incorporated herein in its entirety by reference. The multilayer films disclosed in Giori include an odor barrier layer formed from amorphous polyamide modified with a functionalized polyolefin, for example, maleated ethylene-ethyl acrylate copolymer. The odor barrier layer formed from such modified amorphous polyamide has reduced rigidity and rustling noise when compared to non-modified amorphous polyamides. However, the sound dampening capability of the odor barrier layers formed of the amorphous polyamide modified with a functionalized polyolefin is still low.

Because of the inherent severe medical, social, and personal concerns related to the need for use of an ostomy appliance, improvements in ostomy appliances are desired. Any appreciable improvement in such ostomy appliances to provide greater discretion and privacy is of great importance in the quality of life of the increasing number of ostomy patients. Thus, further improvements in sound absorbing and quietness properties of a multilayer film for ostomy appliances are highly desirable. The present disclosure provides multilayer films having improved sound absorbing and quietness properties according to various embodiments to enhance sound insulating properties of ostomy appliances.

BRIEF SUMMARY

Multilayer films having improved quietness and sound absorbing properties are provided according to various embodiments of the present disclosure. Specifically, the multilayer film includes an odor barrier layer that provides sound absorbing properties and produces less rustling noise in addition to providing excellent odor barrier properties. Such an odor barrier layer may be formed from a polyamide modified with a functionalized sound dampening resin.

In one aspect, a multilayer film comprising an odor barrier layer having sound dampening properties is provided. The odor barrier layer is formed from a polyamide modified with a functionalized vinyl-bond rich triblock copolymer.

In some embodiments, the vinyl-bond rich triblock copolymer may be a vinyl-bond rich styrene-isoprene-styrene (SIS) block copolymer or a vinyl-bond rich styrene-ethylene-propylene-styrene (SEPS) block copolymer, in which the vinyl-bond rich triblock copolymer is functionalized with maleic anhydride or epoxy, and reacted with a polyamide to provide the modified polyamide.

Preferably, the vinyl-bond rich triblock copolymer has a glass transition temperature between about −20° C. and about 20° C., and a temperature at tangent delta peak between about −10° C. and about 30° C., and a tangent delta value at room temperature between about 0.30 and about 1.5. Further, the polyamide is preferably an amorphous polyamide.

In one embodiment, the odor barrier layer may be formed from a blend comprising about 85 wt. % of amorphous polyamide and about 15 wt. % of a vinyl-bond rich SIS block copolymer functionalized with a maleic anhydride, in which the vinyl-bond rich SIS block copolymer has a glass transition temperature of about 8° C., a temperature at tangent delta peak of about 20° C., and a tangent delta of about 1.2 at room temperature.

In another embodiment, the odor barrier layer may be formed from a blend comprising about 85 wt. % of amorphous polyamide and about 15 wt. % of a vinyl-bond rich SIS block copolymer functionalized with a maleic anhydride, in which the vinyl-bond rich SIS block copolymer has a glass transition temperature of about −13° C., a temperature at tangent delta peak of about −3° C., and a tangent delta of about 0.7 at room temperature.

Yet in another embodiment, the odor barrier layer may be formed from a blend comprising about 85 wt. % of amorphous polyamide and about 15 wt. % of a vinyl-bond rich SEPS block copolymer functionalized with a maleic anhydride, in which the vinyl-bond rich SEPS block copolymer has a glass transition temperature of about −15° C., a temperature at tangent delta peak of about −5° C., and a tangent delta of about 0.45 at room temperature.

In some embodiments, other layers of the multilayer film may also include a sound dampening resin, such as a vinyl-bond rich triblock copolymer.

Further, the multilayer film may have various film constructions. For example, the multilayer film may be a five-layer film having an outer layer/tie layer/odor barrier layer/tie layer/outer layer construction or an outer layer/inner layer/tie layer/odor barrier layer/tie layer construction, or a four-layer film having an outer layer/tie layer/odor barrier layer/tie layer construction, or a six-layer film having an outer layer/inner layer/tie layer/odor barrier layer/tie layer/outer layer construction, or a seven-layer film having an outer layer/inner layer/tie layer/odor barrier layer/tie laver/inner laver/outer layer construction. In other embodiments, the multilayer film may include less than four layers or more than seven layers, and may have various different film constructions.

In some embodiments, at least one of the outer layers may be a seal layer comprising ethylene vinyl acetate (EVA) copolymer, ethylene methyl acrylate (EMA) copolymer, ethylene alpha olefin copolymer, olefin block copolymer (OBC), or ethylene-propylene (EP) copolymer or blend thereof, and each of the tie layer is formed from a maleated polyolefin. The inner layers may comprise EVA, EMA, ethylene olefin copolymer, OBC, or EP copolymer, or blends thereof.

In another aspect, an ostomy pouch including a first wall and a second wall is provided. The first wall and the second wall are sealed along their peripheral edges to define a cavity, in which at least one of the first wall and the second wall is formed from any of the aforementioned multilayer film.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
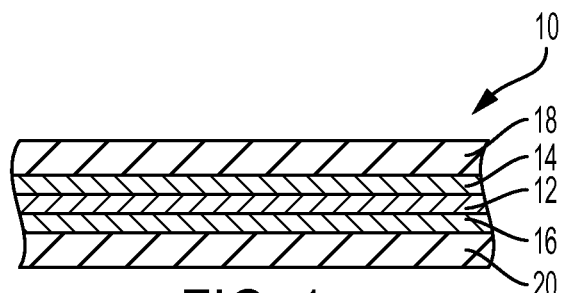
FIG. 1 is a cross-sectional illustration of a five-layer film according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated.

FIG. 1 is a cross-sectional illustration of a multilayer film 10 including an odor barrier layer having sound dampening properties according to an embodiment. The multilayer film 10 is a five-layer film including an odor barrier layer 12, two tie layers 14, 16, and two outer layers 18, 20. As shown, each of the tie layers 14, 16 is arranged between the odor barrier layer 12 and the outer layers 18, 20, respectively, to facilitate adhesion between the odor barrier layer 12 and the outer layers 18, 20.

The odor barrier layer 12 is formed from a polymeric blend comprising a polyamide and a sound dampening resin. For example, the odor barrier layer 12 may be formed from a blend comprising a polyamide and a vinyl-bond rich triblock copolymer, such as a vinyl-bond rich styrene-isoprene-styrene (SIS) block copolymer (e.g. Hybrar® 5125 or 5127 from Kuraray Co. Ltd.) or a vinyl-bond rich styrene-ethylene-propylene-styrene (SEPS) block copolymer (e.g. Hybrar® 7125). In such embodiments, the vinyl-bond rich triblock copolymer may be functionalized with maleic anhydride or epoxy and reacted with a polyamide to modify the polyamide. Preferably, the vinyl-bond rich triblock copolymer having suitable sound dampening properties has a glass transition temperature greater than about $-25°$ C., more preferably between about $-20°$ C. and about $20°$ C., and a temperature at tangent delta peak greater than about $-15°$ C., more preferably between about $-10°$ C. and about $30°$ C., and a tangent delta value at room temperature greater than about 0.30, more preferably between about 0.40 and about 1.5.

In some embodiments, the odor barrier layer 12 may be formed from a blend comprising about 70% by weight (wt. %) to about 95 wt. % of amorphous polyamide (nylon) and about 5 wt. % to about 30 wt. % of functionalized vinyl-bond rich triblock copolymer. For example, the blend comprises about 85 wt. % of amorphous polyamide and about 15 wt. % of a vinyl-bond rich triblock copolymer functionalized with maleic anhydride, such as maleated vinyl-bond rich SEPS block copolymer.

Polyamides suitable for the odor barrier layer 12 include amorphous polyamides having a partially aromatic structure, which are typically produced by the condensation of an aliphatic diamine with an aromatic diacid, or combination of diacids, in molar amounts equivalent to the diamine used. Examples of such a polyamide include a polyamide resin marketed as Selar® PA3426 by DuPont Company, which is substantially amorphous with a density of about 1.19 grams per cubic centimeter (g/cc) and a glass transition temperature (dry) of about $127°$ C. It has high melt strength and can be used under a broader range of processing conditions than conventional crystalline nylons. Selar® PA3426 is produced by the condensation of hexamethylenediamine, terephthalic acid, and isophthalic acid such that 65% to 80% of the polymer units are derived from hexamethylene isophthalamide. Another amorphous polyamide example is Grivory®, such as Grivory® G21, which is commercially available from EMS-Chemie of Sumter, S.C. Grivory® G21 has a density of about 1.18 g/cc and a glass transition temperature (dry) of about $128°$ C.. Grivory® HB5299, which has a density of about 1.2 g/cc and a glass transition temperature (dry) of about $95°$ C. and a melting point temperature of about $219°$ C., is also a suitable amorphous polyamide.

In one embodiment, the odor barrier layer 12 is formed from a blend comprising about 85 wt. % of amorphous polyamide and about 15 wt. % of a functionalized vinyl-bond rich SIS block copolymer having a glass transition temperature of about $8°$ C., a temperature at tangent delta peak of about $20°$ C., and a tangent delta of about 1.2, for example, Hybrar® 5127 resin functionalized with maleic anhydride. In another embodiment, the odor barrier layer 12 is formed from a blend comprising about 85 wt. % of amorphous polyamide and about 15 wt. % of a functionalized vinyl-bond rich SIS block copolymer having a glass transition temperature of about $-13°$ C., a temperature at tangent delta peak of about $-3°$ C., and a tangent delta of about 0.7, for example, Hybrar® 5125 resin functionalized with maleic anhydride. In yet another embodiment, the odor barrier layer 12 is formed from a blend comprising about 85 wt. % of amorphous polyamide and about 15 wt. % of a functionalized vinyl-bond rich SEPS block copolymer having a glass transition temperature of about $-15°$ C., a temperature at tangent delta peak of about $-5°$ C., and a tangent delta of about 0.45, for example, Hybrar® 7125 resin functionalized with maleic anhydride.

The tie layers may be provided adjacent the odor barrier layer to facilitate adhesion of the odor barrier layer to the other layers of the multilayer film. In the embodiment of FIG. 1, the tie layer 14 is arranged between the odor barrier layer 12 and the outer layer 18, while the tie layer 16 is arranged between the odor barrier layer 12 and the outer layer 20. The tie layers 14, 16 may be formed from a same material or different materials depending on the composition of the odor barrier layer 12 and the outer layers 18, 20. Suitable materials for the tie layers 14, 16 include maleated polyolefins, such as a maleated ethylene methyl acrylate copolymers (EMA-MAH) having maleic anhydride present at about 0.3 wt. % and methyl acrylate present at about 20 wt. % of the resin. One such material is available from Arkema, Inc. as Lotader® 4503. In one embodiment, the tie layers 14, 16 are formed from a blend comprising 80 wt. % EMA (Lotryl® 18MA02 from Arkema, Inc.) and 20 wt. % maleated compound (Bynel®CXA41E710 from DuPont.)

In some embodiments, the tie layers 14, 16 may also provide sound absorbing properties. In such embodiments, the tie layer 46 may comprise a vinyl-bond rich triblock copolymer, such as Hybrar® to enhance mechanical properties and sound absorbing properties of the film 10. For example, the tie layers 14, 16 may be formed from a blend of a vinyl-bond rich SEPS block copolymer (e.g. Hybrar® 7125) and a maleated compound (such as Bynel®CXA41E710).

The outer layers 18, 20 may be formed from the same material or different materials. Preferably, at least one of the outer layers 18, 20 is a seal layer having suitable heat sealability, such that the seal layers may be heat sealed together to form a pouch. Suitable materials for the outer layers 18, 20 include ethylene based polymers, such as copolymers of ethylene with vinyl esters, e.g. ethylene vinyl acetate (EVA) and ethylene methyl acrylate (EMA), ethylene alpha olefin copolymers (ethylene based plastomers), ethylene based elastomers (olefin block copolymers, OBC), and ethylene-propylene (EP) copolymers (PP-elastomer), and blends thereof. Suitable EVA copolymers include those containing about 5 wt. % to 35 wt. % vinyl acetate, preferably about 18 wt. % vinyl acetate. One such EVA copolymer is available from ExxonMobil as product Escorene® Ultra FL00218. Such EVA copolymers may have a melting point temperature of 86° C. and a Shore A hardness of about 91. EVA copolymers are known to exhibit the necessary characteristics for joining to another EVA member, as by heat sealing, to provide an air-tight, liquid-tight seal at the joint or seal. EVA copolymer may be blended to facilitate formation and film extrusion. For example, an EVA blend may contain about 98 wt. % EVA copolymer, and about 2 wt. % anti-block and slip additives in an EVA carrier. One such additive is available from A. Schulman Inc., as Polybatch® SAB-1982VA.

Suitable EMA copolymers include about 5 wt. % to about 35 wt. % methyl acrylate, and preferably about 15 wt. % to about 30 wt. % methyl acrylate. One such EMA copolymer is Lotryl®28AM02 supplied by Arkema Inc. This copolymer has a melting point of about 83° C. and specific gravity of about 0.841. EMA copolymers may be blended with anti-block and/or slip additives in an EVA carrier. One such suitable additive is the aforementioned Polybatch® SAB-1982VA. The blend may contain 98 wt. % EMA copolymer, and about 2 wt. % Polybatch® SAB-1982VA anti-block and slip additive.

Another suitable material for the outer layers 18, 20 is ethylene alpha olefin copolymers (ethylene based plastomers). An example of suitable ethylene alpha olefin copolymers is Exact® 0203 resin, supplied by ExxonMobil Corporation, which has a specific gravity of about 0.88, a Shore A hardness of about 95, a melting point temperature of about 95° C., and specific gravity of about 0.902. This resin is designed for both monolayer and multilayer co-extruded cast film applications and is suitable in applications that require toughness and heat sealing performance.

Still another suitable material for the outer layers 18, 20 is ethylene based elastomers (olefin block copolymers, OBC), for example, Infuse® 9107 supplied by Dow Chemical. This material has a specific gravity of about 0.866, a Shore A hardness of about 60 and a melting point of about 121° C.

Still another suitable material for the outer layers 18, 20 is an ethylene-propylene copolymer (PP-elastomer) resin. It has a low modulus and thus exhibits low noise characteristics. It has excellent compatibility with polypropylene (PP) and polyethylene (PE). Preferably, ethylene-propylene copolymers include about 6 wt. % to about 18 wt. % ethylene. An example of suitable ethylene-propylene copolymers is Versify®2200 available from Dow Chemical. This resin is a PP-elastomer including about 9 wt. % ethylene and has melting point of about 82° C., a Shore A hardness of about 94 and a Shore D hardness of about 42. It has a specific gravity of about 0.878. Another example is Vistamaxx® 3980FL from Exxon, which is a PP-elastomer including about 8.5 wt. % ethylene.

Polymer blends comprising EVA copolymer, EMA copolymer, ethylene alpha olefin copolymers (ethylene based plastomers), ethylene based elastomers (olefin block copolymers, OBC), and ethylene-propylene (EP) copolymers (PP-elastomer) are also suitable for the outer layers. Examples include, but are not limited to, a blend of EVA copolymer (Escorene®FL00218 present at 49 wt. %) and ethylene-propylene copolymer (PP-elastomer, Versify®2200 present at 49 wt. %) with anti-block and slip additives, and a blend of EMA copolymer (Elvaloy®1330AC present at 49 wt. %) and PP-elastomer (Versify®2200 present at 49 wt. %) also with anti-block and slip additives. Blends of various EP copolymer resins are also suitable, for example, blends of Versify®2200 and Versify®3400, which is a similar EP copolymer resin, but has a higher melting point of about 97° C., a Shore A hardness of 72 and a Shore D hardness of 22, and a specific gravity of about 0.865. Suitable blends can have ratios of about 50 wt. % of Versify®2200 to about 75 wt. % of Versify®2200 of the blend. PP-elastomers such as Versify®, Vistamaxx®, and Notio® from Mitsui, and PP-EP rubber such as Adflex® Q100F from LyondellBasell are also suitable.

In one embodiment, the outer layers 18, 20 may be formed from a blend including about 49 wt. % EVA copolymer (e.g. Escorene® Ultra FL00218), about 49 wt. % EP copolymer (e.g. Vistamaxx® 3980FL), and about 2 wt. % anti-block and slip additive (e.g. Polybatch® SAB-1982VA.)

The outer layers 18, 20 may also provide sound absorbing properties. In such an embodiment, the outer layers 18, 20 may comprise a vinyl-bond rich triblock copolymer, such as Hybrar® to enhance mechanical properties and sound absorbing properties. For example, the outer layers 18, 20 may be formed from a blend of vinyl-bond rich styrene-isoprene-styrene (SIS) block copolymer (e.g. Hybrar® 5127), PP-elastomer (e.g. Vistamaxx®), and EMA copolymer (e.g. Lotryl® 20MA08).

Figure 2:
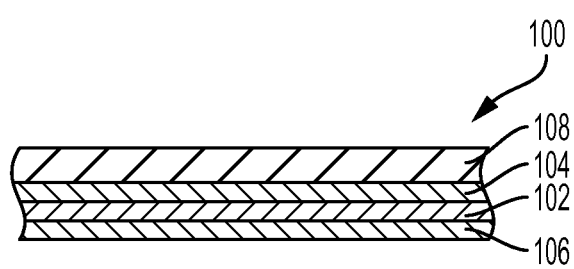
FIG. 2 is a cross-sectional illustration of a four-layer film according to an embodiment.
Figure 5:
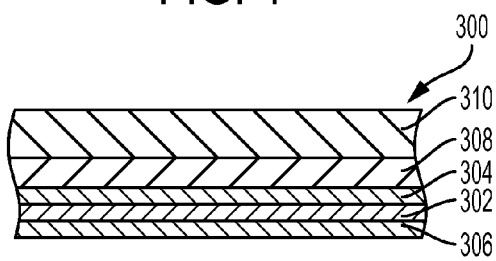
FIG. 5 is a cross-sectional illustration of a five-layer film according to another embodiment.

Although, the multilayer film 10 of FIG. 1 is shown as a five-layer film having an outer layer/tie layer/odor barrier layer/tie layer/outer layer construction, in other embodiments, a multilayer film may have a different film construction or may have more than five layers or less than five layers. For example, a four-layer film 100 including an odor barrier layer having sound dampening properties is shown in FIG. 2. The four-layer film 100 has an outer layer 108/tie layer 104/odor barrier layer 102/tie layer 106 construction. FIG. 5 illustrates a five-layer film having a different film construction. The five-layer film 300 has an outer layer 310/inner layer 308/tie layer 304/odor barrier layer 302/tie layer 306 construction.

Figure 3:
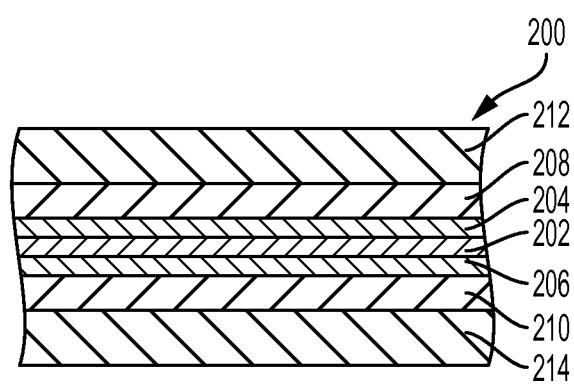
FIG. 3 is a cross-sectional illustration of a seven-layer film according to an embodiment.

FIG. 3 is a cross-sectional illustration of a multilayer film 200 including an odor barrier layer having sound dampening properties according to another embodiment. The multilayer film 200 is a seven-layer film including an odor barrier layer 202, two tie layers 204, 206, two inner layers 208, 210, and two outer layers 212, 214. The seven-layer film 200 is similarly constructed as the five-layer film 100 of FIG. 100, except the inner layers 208, 210 are provided between the tie layers 204, 206 and the outer layers 212, 214.

As shown, the inner layer 208 is arranged between the tie layer 204 and the outer layer 212, while the inner layer 210 is arranged between the tie layer 206 and the outer layer 214. The inner layers 208, 212 may provide improved film properties. For example, the inner layers 208, 212 may impart additional mechanical properties, such as improved tear strength to the multilayer film 200. The aforementioned materials for the outer layers 18, 20 of the five-layer film 10 are also suitable for the inner layers 208, 210. For example, ethylene based polymers, such as copolymers of ethylene with vinyl esters, e.g. EVA copolymer and EMA copolymer, ethylene alpha olefin copolymers (ethylene based plastomers), ethylene based elastomers (olefin block copolymers, OBC), and ethylene-propylene (EP) copolymers (PP-elastomer), and blends thereof are suitable for the inner layers 208, 210.

In one embodiment, the inner layers 208, 210 may be formed from a blend including about 65 wt. % EP copolymer (e.g. Vistamaxx® 3980FL) and about 35 wt. % PP-EP rubber (e.g. Adflex® Q100F.)

In some embodiments, the inner layers 208, 210 may also provide sound absorbing properties. In such an embodiment, the inner layers 208, 210 may comprise a vinyl-bond rich triblock copolymer, such as Hybrar®, to enhance mechanical properties and sound absorbing properties of the multilayer film 200. For example, the inner layers 208, 210 may be formed from a blend of vinyl-bond rich styrene-ethylene-propylene-styrene (SEPS) block copolymer (e.g. Hybrar®7125) and PP-elastomer (Vistamaxx®).

Figure 6:
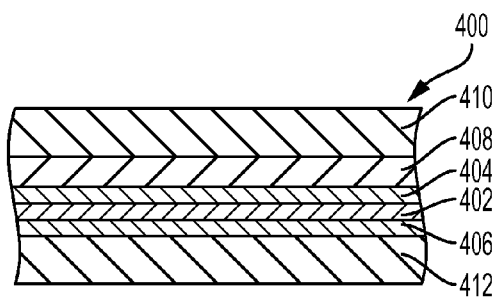
FIG. 6 is a cross-sectional illustration of a six-layer film according to yet another embodiment.

FIG. 6 is a cross-sectional illustration of a multilayer film 400 including an odor barrier layer having sound dampening properties according to yet another embodiment. The multilayer film 400 is a six-layer film including an outer layer 410/inner layer 408/tie layer 404/odor barrier layer 402/tie layer 406/outer layer 412.

Figure 4:
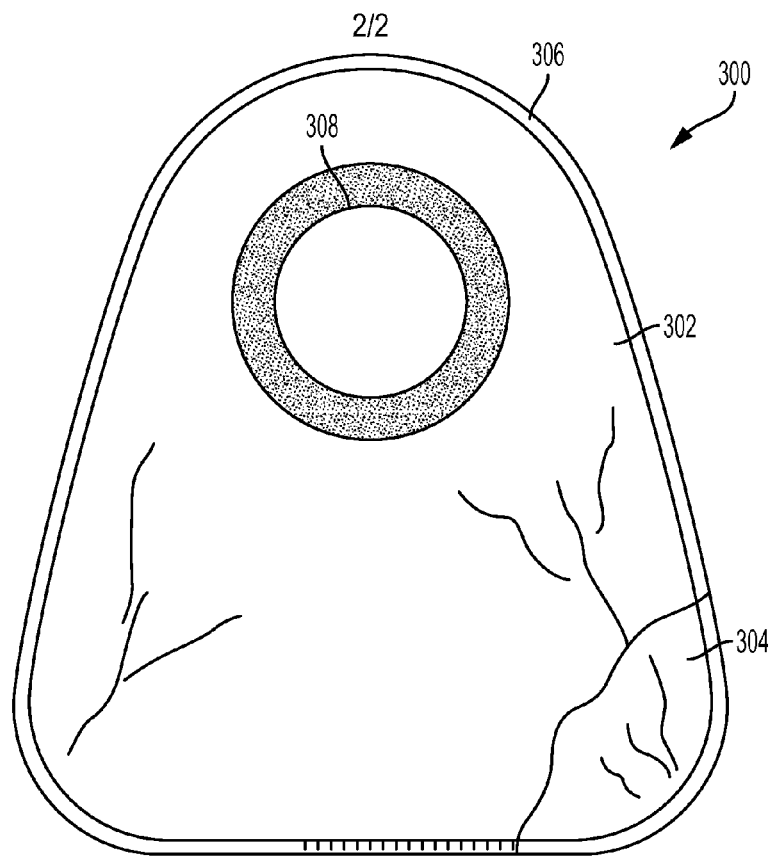
FIG. 4 is an illustration of an exemplary ostomy pouch.

The multilayer films according to various embodiments of the present disclosure may be used to manufacture, for example, an ostomy pouch, such as that illustrated in FIG. 4. The pouch 300 is formed from two sheets of film 302, 304 that are heat or otherwise sealed, as at 306 to one another to form an air-tight, liquid-tight pouch 300. An opening 308 in the pouch permits the accommodation of, for example, a surgically formed stoma (not shown) for the inflow of waste into the pouch. The configuration of such a pouch can be in accordance with the disclosure of the aforementioned U.S. Pat. No. 7,270,860 to Giori. Other configurations of pouches or other containers, as well as other uses, will be recognized by those skilled in the art.

What is claimed is:

1. A multilayer film comprising an odor barrier layer having sound dampening properties, wherein the odor barrier layer is formed from a blend comprising about 85 wt. % polyamide and about 15 wt. % of a vinyl-bond rich triblock copolymer functionalized with a maleic anhydride, wherein the vinyl-bond rich triblock copolymer is a vinyl-bond rich styrene-isoprene-styrene (SIS) block copolymer having a chemical structure

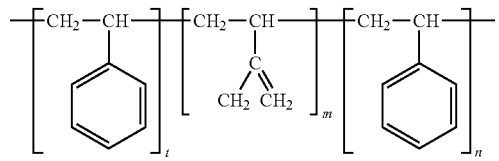

or a vinyl-bond rich styrene-ethylene-propylene-styrene (SEPS) block copolymer having a chemical structure

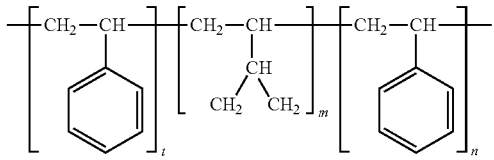

2. The multilayer film of claim 1, wherein the polyamide is an amorphous polyamide.

3. The multilayer film of claim 1, wherein the vinyl-bond rich SIS block copolymer has a glass transition temperature of about 8° C., a temperature at tangent delta peak of about 20° C., and a tangent delta of about 1.2 at room temperature.

4. The multilayer film of claim 1, wherein the vinyl-bond rich SIS block copolymer has a glass transition temperature of about −13° C., a temperature at tangent delta peak of about −3° C., and a tangent delta of about 0.7 at room temperature.

5. The multilayer film of claim 1, wherein the vinyl-bond rich SEPS block copolymer has having a glass transition temperature of about −15° C., a temperature at tangent delta peak of about −5° C., and a tangent delta of about 0.45 at room temperature.

6. The multilayer film of claim 1, wherein the multilayer film is a five layer film having additional layers forming an outer layer/tie layer/odor barrier layer/tie layer/outer layer construction.

7. The multilayer film of claim 1, wherein the multilayer film is a five layer film having additional layers forming an outer layer/inner layer/tie layer/odor barrier layer/tie layer construction.

8. The multilayer film of claim 1, wherein the multilayer film is a four layer film having additional layers forming an outer layer/tie layer/odor barrier layer/tie layer construction.

9. The multilayer film of claim 1, wherein the multilayer film is a seven layer film having additional layers forming an outer layer/inner layer/tie layer/odor barrier layer/tie layer/inner layer/outer layer construction.

10. The multilayer film of claim 1, wherein the multilayer film is a six layer film having additional layers forming an outer layer/inner layer/tie layer/odor barrier layer/tie layer/outer layer construction.

11. The multilayer film of claim 1, wherein the multilayer film further includes at least one outer layer and at least one tie layer, wherein the at least one outer layer is a seal layer comprising ethylene vinyl acetate (EVA) copolymer, ethylene methyl acrylate (EMA) copolymer, ethylene alpha olefin copolymer, olefin block copolymer (OBC), or ethylene-propylene (EP) copolymer, or blends thereof and the at least one tie layer is formed from a maleated polyolefin.

12. The multilayer film of claim 1, wherein the multilayer film includes at least one inner layer comprising EVA, EMA, ethylene olefin copolymer, OBC, or EP copolymer.

13. The multilayer film of claim 1, wherein at least one additional layer comprises a sound dampening resin.

14. An ostomy pouch, comprising:
a first wall;
a second wall, wherein the first wall and the second wall are sealed along their peripheral edges to define a cavity;
wherein at least one of the first wall and the second wall is formed from the multilayer film of claim 1.

* * * * *

UNITED STATES PATENT AND TRADEMARK OFFICE
CERTIFICATE OF CORRECTION

PATENT NO. : 10,470,917 B2
APPLICATION NO. : 15/301829
DATED : November 12, 2019
INVENTOR(S) : Moh-Ching Oliver Chang Page 1 of 1

It is certified that error appears in the above-identified patent and that said Letters Patent is hereby corrected as shown below:

In the Specification

1. In Column 3, Line 9, delete "laver/inner laver/outer" and insert -- layer/inner layer/outer --, therefor.
2. In Column 5, Line 65, delete "Lotryl®28AM02" and insert -- Lotryl®18AM02 --, therefor.
3. In Column 7, Line 25, delete "Fig. 100," and insert -- Fig. 2, --, therefor.

In the Claims

4. In Column 8, Lines 20-25, in Claim 1, delete " 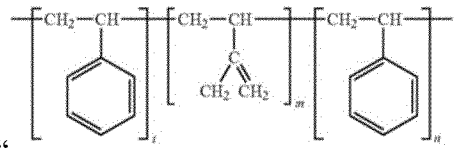 " and insert -- 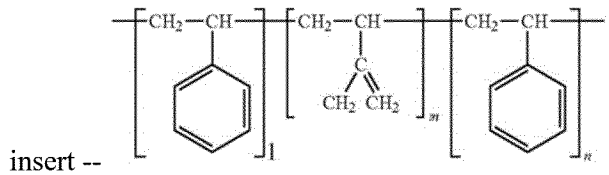 --, therefor.

5. In Column 8, Lines 32-37, in Claim 1, delete " 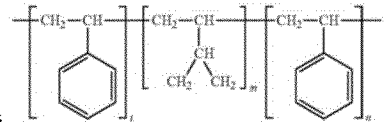 " and insert -- 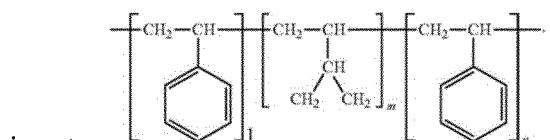 --, therefor.

Signed and Sealed this
Seventh Day of July, 2020

Andrei Iancu
*Director of the United States Patent and Trademark Office*